United States Patent
Yu et al.

(10) Patent No.: US 10,010,875 B2
(45) Date of Patent: Jul. 3, 2018

(54) METHOD FOR PREPARING COPPER-ZINC-BASED CATALYST USED IN SYNTHESIS OF METHANOL THROUGH $CO_2$ HYDROGENATION

(71) Applicants: China Petroleum & Chemical Corporation, Beijing (CN); Research Institute of Nanjing Chemical Industry Gr, Nanjing (CN)

(72) Inventors: Yang Yu, Nanjing (CN); Aixiang Hao, Nanjing (CN); Haibo Chen, Nanjing (CN); Shixin Wei, Nanjing (CN); Yusheng Yin, Nanjing (CN); Tianming Xie, Nanjing (CN); Jian He, Nanjing (CN); Chunpeng Mao, Nanjing (CN); Jiedong Tan, Nanjing (CN)

(73) Assignees: CHINA PETROLEUM & CHEMICAL CORPORATION, Beijing (CN); RESEARCH INSTITUTE OF NANJING CHEMICAL INDUSTRY GROUP, Nanjing (CN)

( * ) Notice: Subject to any disclaimer, the term of this patent is extended or adjusted under 35 U.S.C. 154(b) by 95 days.

(21) Appl. No.: 14/928,345

(22) Filed: Oct. 30, 2015

(65) Prior Publication Data
US 2016/0121306 A1 May 5, 2016

(30) Foreign Application Priority Data

Oct. 30, 2014 (CN) .......................... 2014 1 0604941

(51) Int. Cl.
*B01J 23/80* (2006.01)
*B01J 37/03* (2006.01)
*B01J 35/00* (2006.01)
*C07C 29/154* (2006.01)
*B01J 37/04* (2006.01)
*B01J 23/83* (2006.01)
*B01J 37/34* (2006.01)
*B01J 37/10* (2006.01)
*B01J 37/18* (2006.01)
*B01J 37/06* (2006.01)
*B01J 37/00* (2006.01)
*B01J 37/08* (2006.01)

(52) U.S. Cl.
CPC .............. *B01J 23/80* (2013.01); *B01J 23/83* (2013.01); *B01J 35/0053* (2013.01); *B01J 37/03* (2013.01); *B01J 37/031* (2013.01); *B01J 37/04* (2013.01); *B01J 37/343* (2013.01); *C07C 29/154* (2013.01); *B01J 35/002* (2013.01); *B01J 37/0009* (2013.01); *B01J 37/06* (2013.01); *B01J 37/08* (2013.01); *B01J 37/10* (2013.01); *B01J 37/18* (2013.01); *B01J 2523/00* (2013.01); *Y02P 20/52* (2015.11)

(58) Field of Classification Search
None
See application file for complete search history.

(56) References Cited

U.S. PATENT DOCUMENTS 3,971,735 A * 7/1976 Asano ...................... B01J 23/80
502/202

OTHER PUBLICATIONS

Li and Inui (Enhancement in methanol synthesis activity of copper/zinc/aluminum oxide catalyst by ultrasonic treatment during the course of preparation procedure, Appl Cata A: Gen 139(1996)87-96).*
Arena et al., "Synthesis, characterization and activity pattern of Cu—ZnO/ZrO2 catalysts in the hydrogenation of carbon dioxide to methanol", Journal of Catalysis, Elsevier, 2007, vol. 249, pp. 185-194.
Chu et al., "Surfactant-assisted preparation of Cu/ZnO/Al2O3 catalyst for methanol synthesis from syngas", Journal of Molecular Catalysis A: Chemical, Elsevier, 2013, vol. 366, pp. 48-53.
Olah et al., "Chemical Recycling of Carbon Dioxide to Methanol and Dimethyl Ether: From Greenhouse Gas to Renewable, Environmentally Carbon Neutral Fuels and Synthetic Hydrocarbons", Journal of Organic Chemistry, American Chemical Society, 2009, vol. 74, No. 2, pp. 487-498.

* cited by examiner

*Primary Examiner* — Melvin C. Mayes
*Assistant Examiner* — Michael Forrest
(74) *Attorney, Agent, or Firm* — Buchanan Ingersoll & Rooney PC

(57) ABSTRACT

Disclosed is a method for preparing a copper-zinc-based catalyst used in synthesis of methanol through $CO_2$ hydrogenation, and ultrasonic waves are used for control over crystalline phase's composition of a catalyst precursor. Further related to is a catalyst prepared by such a method. An amount of aurichalcite in an active catalyst precursor can be improved through the method, and the specific surface area of the metal copper in a reduced state catalyst is high. The catalyst presents high activity and hydrothermal stability, and promotes high space time yield of methanol in the synthesis of methanol through $CO_2$ hydrogenation.

18 Claims, No Drawings

METHOD FOR PREPARING COPPER-ZINC-BASED CATALYST USED IN SYNTHESIS OF METHANOL THROUGH $CO_2$ HYDROGENATION

CROSS-REFERENCE TO RELATED APPLICATIONS

The present application claims benefit of Chinese patent application 201410604941.6 filed on Oct. 30, 2014, the entirety of which is incorporated herein by reference.

FIELD OF THE INVENTION

The present disclosure relates to the technical field of preparation of a catalyst, and in particular, to a method for preparing a catalyst used in methanol synthesis.

BACKGROUND OF THE INVENTION

Rapid development of modern industries, and constant increase in the number of automobiles have caused an evergrowing concentration of carbon dioxide ($CO_2$) in atmosphere, and further lead to environment pollution and extreme climates, which have been drawing increasing high attention of the countries in the word. Therefore, how to reduce the concentration of $CO_2$ in atmosphere and maintain an ecofriendly one has become the global concern.

George Andrew Olah, the famous organic chemist and Nobel Prize winner of chemistry, had proposed the concept of "Methanol Economy", that is, $CO_2$ captured from the atmosphere catalytically reacts with hydrogen prepared by using non-fossil energy to synthesize methanol, which can serve as the energy to reserve instead of fossil energies, as fuels itself and as raw material in the synthesis of hydrocarbons and their down-stream products. Methanol Economy will be an effective solution to oil gas and energy problems in the future. (*J. Org. Chem.*, 2009, 74(2): 487-498.) Nobel Prize winner of physics, Carol Rubbia, had also proposed to use a procedure of preparing methanol through $CO_2$ hydrogenation to replace the currently popular capture and storage of carbon, so as to reduce emissions and meanwhile provide raw materials to the development of the industry. US Carbon Science Inc. has put forward a three-step procedure to produce a fuel oil with $CO_2$, wherein $CO_2$ in flue gases is used as a raw material, and saline electrolysis is used to provide necessary hydrogen.

There are numerous correlated studies and reports on the technology of synthesis of methanol through hydrogenation of $CO_2$ over the world. However, this technology has still been confronted with some technical difficulties for industrialization thereof, among which the most important comes to research in the development of high-performance catalysts. It is not easy for $CO_2$ to participate in a chemical reaction because the chemical-bond energy of $CO_2$ is rather high. As a result, it is necessary for the reaction in synthesis of methanol through $CO_2$ hydrogenation to be performed in the presence of a high-performance catalyst. Conventional catalyst Cu—ZnO—$Al_2O_3$ used in synthesis of methanol does not present very high performance while being used in $CO_2$ hydrogenation to methanol. It is widely believed that, the active precursor of a Cu—ZnO-based catalyst used in CO (or $CO_2$) hydrogenation to methanol should be in the form of a Cu—Zn double salt before being roasted, including $(Cu,Zn)_2CO_3(OH)_2$ (rosasite crystalline phase) and $(Cu, Zn)_5(CO_3)_2(OH)_6$ (aurichalcite crystalline phase). The crystalline phase in the precursor of the catalyst prepared through the conventional coprecipitation method and used in synthesis of methanol, before being roasted, is substantially in the form of the rosasite crystalline phase (*J. Mol. Catal., A-Chemical*, 2013, 366: 48-53.), which, as the active precursor used in synthesis of methanol through $CO_2$ hydrogenation, is not an optimum active precursor in the synthesis of methanol through $CO_2$ hydrogenation although presents catalytic performance to a certain degree. There are also some researchers believe that, due to generation of a large amount of water in the synthesis of methanol through $CO_2$ hydrogenation, and hydrophilic nature of $Al_2O_3$, the catalyst, readily influenced by the molecules of water, would have decreased mechanical strength, modified active sites, etc. (*J. Catal.*, 2007, 249(2): 185-194.) Therefore, the studies on improvement of catalytic performance of copper-zinc-based catalysts in the synthesis of methanol through $CO_2$ hydrogenation mainly focus on the preparation method of the catalysts, and on selection of promoters and carriers. The purpose thereof is to enable controlling over formation of the crystalline phase of the active precursor of the catalyst used in the synthesis of methanol through $CO_2$ hydrogenation, and to improve catalytic performance and hydrothermal stability of the catalyst.

SUMMARY OF THE INVENTION

The purposes of the present disclosure are to provide a method for preparing a copper-zinc-based catalyst and a catalyst prepared thereby. According to the method of the present disclosure, catalytic performance and hydrothermal stability of the catalyst used in the synthesis of methanol through hydrogenation of $CO_2$ can be improved.

One of the objectives of the present disclosure is to provide a method for preparing a copper-zinc-based catalyst used in synthesis of methanol through $CO_2$ hydrogenation, comprising the following steps:

step S1: preparing an aqueous solution containing a copper salt, a zinc salt, and a metal salt promoter, and blending said aqueous solution and an aqueous solution of a precipitator, to produce a first feed liquid for direct reaction under radiation of ultrasonic waves, thereby generating a first reaction product, which goes through aging, solid-liquid separation, and washing to produce a parent body;

step S2: preparing a solution of a carrier precursor, which is blended with the aqueous solution of a precipitator, to produce a second feed liquid for direct reaction under radiation of ultrasonic waves, thereby generating a second product, which goes through stirring, solid-liquid separation, and washing to produce a carrier material; and step S3: blending and stirring the parent body and the carrier material, to generate a third product, which goes through solid-liquid separation, washing, and drying to produce a catalyst precursor, followed by roasting of the catalyst precursor to obtain the catalyst.

According to the method provided in the present disclosure, radiation of ultrasonic waves can be imposed on parallel precipitating procedures respectively, to control crystalline phase's composition of the catalyst precursor obtained. This can significantly improve the content of aurichalcite crystalline phase, thereby improving catalytic performance and hydrothermal stability of the catalyst obtained.

According to one specific embodiment of the method of the present disclosure, the ultrasonic waves have a frequency in the range from 20 to 40 kHz, and a power in the range from 50 to 500 W. The ultrasonic waves as defined above can more effectively control the crystalline phase's composition of the precursor obtained.

According to one specific embodiment of the method of the present disclosure, said blending and/or reaction are performed each time at a temperature in the range from 40 to 75° C. Said blending includes the blending performed in steps S1 and S2. And said reaction includes the reactions performed in steps S1 and S2. A pH value at an end of the reaction is controlled within the range from 7 to 8.

According to one specific embodiment of the method of the present disclosure, said blending is performed each time in a blender. Said blending includes the blending performed in steps S1 and S2. Said reaction is performed each time in a reaction tube. And said reaction includes the reactions performed in steps S1 and S2. According to the present disclosure, a small-sized flow mixing device can be further used, which cooperate with the ultrasonic waves in the synthesis of the copper-zinc-based catalyst, so as to enable more accurate control over preparation conditions of the catalyst, and facilitate the adjustment of the crystalline phase's composition of the active catalyst precursor, thereby improving catalytic performance and hydrothermal stability of the catalyst. The small-sized flow mixing device comprises a blender and a reaction tube. The blender has a passage diameter in the range from 50 to 2,000 μm, and a residence time of the first and second feed liquids in the blender ranges from 5 to 1,000 ms. The reaction tube has an inner diameter in the range from 0.5 to 8 mm, and a residence time of the first and second feed liquids in the reaction tube ranges from 5 to 40 min. A feed liquid at an outlet of the reaction tube has a pH value controlled in the range from 7 to 8.

According to one specific embodiment of the method of the present disclosure, said aging is hydrothermal aging. Compared with ordinary aging, hydrothermal aging can further increase an amount of the active crystalline phase in the catalyst precursor. In one specific embodiment, the hydrothermal aging is performed for 4 to 24 hours under airtight conditions at a temperature in the range from 60 to 80° C.

According to one specific embodiment of the method of the present disclosure, main crystalline phase's composition of the catalyst precursor comprises rosasite crystalline phase, aurichalcite crystalline phase, and malachite crystalline phase. The ratio of X-ray diffraction peak intensity of the malachite crystalline phase (at 2θ of about 31.9°) to the sum of X-ray diffraction peak intensity of the rosasite crystalline phase (at 2θ of about 17.3°) and X-ray diffraction peak intensity of the aurichalcite crystalline phase (at 2θ of about 33.0°) is (0.05-0.12):1. And the ratio of the X-ray diffraction peak intensity of the aurichalcite crystalline phase (at 2θ of about 33.0°) to the X-ray diffraction peak intensity of the rosasite crystalline phase (at 2θ of about 17.3°) is (0.25-0.45):1.

According to one specific embodiment of the method of the present disclosure, the aqueous solution containing a copper salt, a zinc salt, and a metal salt promoter, is an aqueous solution of copper-nitrate, zinc-nitrate, and a metal nitrate promoter. An amount of the zinc-nitrate used is known in the art. For example, the zinc-nitrate can be used at such an amount as to enable a molar ratio of copper to zinc in the range from 3:7 to 7:3. The metal salt promoter comprises at least one selected from a group consisting of alkaline earth metal salts and rare earth element salts. An amount of the metal salt promoter used is also known in the art. For example, the metal salt promoter can be used at such an amount as to enable the molar ratio of the promoter to the element of copper in the catalyst to be (0.05-0.1):1. The carrier precursor is a commonly used one in the art and can, for example, be at least one selected from a group consisting of aluminum nitrate, zirconium nitrate, and tetrabutyl titanate. The carrier precursor is used at such an amount that the molar ratio of the carrier in total to the element of copper in the catalyst is (0.1-1):1.

According to one specific embodiment of the method of the present disclosure, the precipitator comprises at least one selected from a group consisting of sodium carbonate, sodium bicarbonate, potassium carbonate, and potassium bicarbonate; or alternatively comprises a mixture of at least one selected from a group consisting of sodium carbonate, sodium bicarbonate, potassium carbonate, and potassium bicarbonate, and at least one selected from a group consisting of sodium hydroxide and potassium hydroxide. In one specific embodiment, the aqueous solution of a precipitator has a concentration of the precipitator in the range from 0.05 to 1 mol/L. An amount of the aqueous solution of the precipitator used is also known in the art. For example, the aqueous solution of the precipitator can be added at such an amount that the pH value at the end of the reaction is controlled within the range from 7 to 8. When the precipitator comprises a mixture of at least one selected from a group consisting of sodium carbonate, sodium bicarbonate, potassium carbonate, and potassium bicarbonate, and at least one selected from a group consisting of sodium hydroxide and potassium hydroxide, the molar ratio of the at least one selected from a group consisting of sodium carbonate, sodium bicarbonate, potassium carbonate, and potassium bicarbonate to the at least one selected from a group consisting of sodium hydroxide and potassium hydroxide is not lower than 1:3.

According to the present disclosure, washing, drying, roasting, and the like in the method are all performed through prior art procedures. For example, the washing can be completed when the electrical conductivity of a solution obtained thereby reaches lower than 10 μS/cm; the blending and stirring in step S3 are performed at a temperature in the range from 40 to 75° C.; and the temperature for roasting is in the range from 300 to 500° C. After aging, especially hydrothermal aging, a turbid liquid turns emerald one. The molding can be performed in a conventional molding procedure, such as graphite-added molding.

A second objective of the present disclosure is to provide another method for preparing a copper-zinc-based catalyst used in synthesis of methanol through $CO_2$ hydrogenation, comprising: preparing a solution containing a copper salt, a zinc salt, a metal salt promoter, and a carrier precursor, and blending said solution and an aqueous solution of a precipitator, to produce a third feed liquid for direct reaction under radiation of ultrasonic waves, thereby generating a product, which goes through stirring, aging, solid-liquid separation, washing, and drying to produce a catalyst precursor, followed by roasting of the catalyst precursor to obtain the catalyst.

According to the method provided in the present disclosure, radiation of ultrasonic waves can be imposed on a reaction stage of a coprecipitation procedure to control crystalline phase's composition of the catalyst precursor obtained. This can significantly improve the content of the aurichalcite crystalline phase, thereby improving catalytic performance and hydrothermal stability of the catalyst obtained.

According to one specific embodiment of the method of the present disclosure, the ultrasonic waves have a frequency in the range from 20 to 40 kHz, and a power in the range from 50 to 500 W. The ultrasonic waves as defined above can more effectively control the crystalline phase's composition of the precursor obtained.

According to one specific embodiment of the method of the present disclosure, said blending and/or reaction are performed each time at a temperature in the range from 40 to 75° C. A pH value at an end of the reaction is controlled within the range from 7 to 8.

According to one specific embodiment of the method of the present disclosure, said blending is performed in a blender. Said reaction is performed in a reaction tube. According to the present disclosure, a small-sized flow mixing device can be further used, which cooperate with radiation of ultrasonic waves in the synthesis of the copper-zinc-based catalyst, so as to enable more accurate control over preparation conditions of the catalyst, and facilitate adjustment of the crystalline phase's composition of the active catalyst precursor, thereby improving catalytic performance and hydrothermal stability of the catalyst. The small-sized flow mixing device comprises a blender and a reaction tube. The blender has a passage diameter in the range from 50 to 2,000 μm, and a residence time of the third feed liquid in the blender ranges from 5 to 1,000 ms. The reaction tube has an inner diameter in the range from 0.5 to 8 mm, and a residence time of the third feed liquid in the reaction tube ranges from 5 to 40 min. A feed liquid at an outlet of the reaction tube has a pH value controlled in the range from 7 to 8.

According to one specific embodiment of the method of the present disclosure, said aging is hydrothermal aging. Compared with ordinary aging, hydrothermal aging can further increase an amount of the active crystalline phase in the catalyst precursor. In one specific embodiment, the hydrothermal aging is performed for 4 to 24 hours under airtight conditions at a temperature in the range from 60 to 80° C.

According to one specific embodiment of the method of the present disclosure, main crystalline phase's composition of the catalyst precursor comprises rosasite crystalline phase, aurichalcite crystalline phase, and malachite crystalline phase, or alternatively comprises rosasite crystalline phase, aurichalcite crystalline phase, and hydrotalcite crystalline phase. The ratio of X-ray diffraction peak intensity of the malachite crystalline phase (at 2θ of about 31.9°) or X-ray diffraction peak intensity of the hydrotalcite crystalline phase (at 2θ of about 11.7°) to the sum of X-ray diffraction peak intensity of the rosasite crystalline phase (at 2θ of about 17.3°) and X-ray diffraction peak intensity of the aurichalcite crystalline phase (at 2θ of about 33.0°) is (0.05-0.12):1. And the ratio of the X-ray diffraction peak intensity of the aurichalcite crystalline phase (at 2θ of about 33.0°) to the X-ray diffraction peak intensity of the rosasite crystalline phase (at 2θ of about 17.3°) is (0.25-0.45):1. When the carrier precursor used contains an aluminum salt, the catalyst precursor obtained contains the hydrotalcite crystalline phase.

According to one specific embodiment of the method of the present disclosure, the solution containing a copper salt, a zinc salt, and a metal salt promoter, is a solution of copper-nitrate, zinc-nitrate, and a metal nitrate promotor. A dosage of the zinc-nitrate is known in the art. For example, the zinc-nitrate can be used at such an amount as to enable a molar ratio of copper to zinc in the range from 3:7 to 7:3. The metal salt promoter comprises at least one selected from a group consisting of alkaline earth metal salts and rare earth element salts. A dosage of the metal salt promoter is also known in the art. For example, the metal salt promoter can be used at such an amount as to enable the molar ratio of the promoter in total to the element of copper in the catalyst to be (0.05-0.1):1. The carrier precursor is a commonly used one in the art and can, for example, be at least one selected from a group consisting of aluminum nitrate, zirconium nitrate, and tetrabutyl titanate. The carrier precursor is used at such an amount that the molar ratio of the carrier in total to the element of copper in the catalyst is (0.1-1):1.

According to one specific embodiment of the method of the present disclosure, the precipitator comprises at least one selected from a group consisting of sodium carbonate, sodium bicarbonate, potassium carbonate, and potassium bicarbonate; or alternatively comprises a mixture of at least one selected from a group consisting of sodium carbonate, sodium bicarbonate, potassium carbonate, and potassium bicarbonate, and at least one selected from a group consisting of sodium hydroxide and potassium hydroxide. In one specific embodiment, the aqueous solution of a precipitator has a concentration of the precipitator in the range from 0.05 to 1 mol/L. A dosage of the aqueous solution of the precipitator is also known in the art. For example, the aqueous solution of the precipitator can be added at such an amount that the pH value at the end of the reaction is controlled within the range from 7 to 8. When the precipitator comprises a mixture of at least one selected from a group consisting of sodium carbonate, sodium bicarbonate, potassium carbonate, and potassium bicarbonate, and at least one selected from a group consisting of sodium hydroxide and potassium hydroxide, the molar ratio of the at least one selected from a group consisting of sodium carbonate, sodium bicarbonate, potassium carbonate, and potassium bicarbonate to the at least one selected from a group consisting of sodium hydroxide and potassium hydroxide is not lower than 1:3.

According to the present disclosure, washing, drying, roasting, molding, and the like in the method are all performed through prior art procedures. For example, the washing can be completed when the electrical conductivity of a solution obtained thereby reaches lower than 10 μS/cm; and the temperature for roasting is in the range from 300 to 500° C. After aging, especially hydrothermal aging, a turbid liquid turns into an emerald one. The molding can be performed in a conventional molding procedure, such as graphite molding. And aging can be performed through stirring for a time at a certain temperature.

A third objective of the present disclosure is to provide a copper-zinc-based catalyst used in the synthesis of methanol through $CO_2$ hydrogenation. The catalyst is reduced to generate a reduced state catalyst, in which a product of a mass percent of the metal copper and a specific surface area of the metal copper is in the range from 10 to 20 m$^2$/g. In one specific embodiment, the catalyst is prepared through the method as described above. The reduction is performed through a conventional reduction procedure. For example, a mixture of $H_2$ and $N_2$ containing 5% of $H_2$ can be used to perform such reduction, with a temperature at an end of the reduction being 240° C.

According to the catalyst of the present disclosure, the molar ratio of copper to zinc is in the range from 3:7 to 7:3. The carrier is a commonly used one, preferably comprising at least one selected from a group consisting of aluminum oxide, zirconium oxide, and titanium oxide. The molar ratio of the carrier in total to the element of copper in the catalyst is (0.1-1):1. And the molar ratio of the promoter in total to the element of copper in the catalyst is (0.05-0.1):1.

The catalyst according to the present disclosure contains a high content of aurichalcite crystalline phase in the precursor thereof; there are active interactive between copper and zinc; and the specific surface area of the metal copper in the reduced state catalyst is high. The catalyst presents high activity and hydrothermal stability, and promotes high space time yield of methanol in the synthesis of methanol through $CO_2$ hydrogenation.

DETAILED DESCRIPTION OF THE EMBODIMENTS

In the following, the present disclosure will be further illustrated through specific examples, which, however, will not limit the present disclosure in any manner.

Test Methods:

1. Characterization of XRD: A powder X-ray diffractometer, Bruker AXS D8 Focus, was used in Powder X-ray Diffraction (XRD) analysis, wherein Cu $K_\alpha$ ($\lambda$=0.15406 nm) was used as a ray source, and an X-ray tube had a working voltage and a working current respectively as 40 kv and 40 mA. The scanning speed and scanned area were respectively 6°/min and 10°<2θ<80°. The average grain sizes of the samples were calculated through the Scherrer equation.

2. Determination of specific surface area: the specific surface area of copper was tested by $N_2O$ chemisorption method.

Example 1 (Comparative Example)

160.9 g of $Cu(NO_3)_2 \cdot 5H_2O$, 115.0 g of $Zn(NO_3)_2 \cdot 6H_2O$, 1.5 g of $Mg(NO_3)_2 \cdot 6H_2O$, and 1.4 g of $Ca(NO_3)_2 \cdot 4H_2O$ were weighed and dissolved into water to prepare an aqueous solution A having a concentration of 0.5 mol/L. An aqueous solution B of $K_2CO_3$ at a concentration of 0.5 mol/L was prepared. After these two solutions were preheated to 70° C., they were simultaneously dropwise added into a container containing 300 mL of deionized water at 70° C., and violently stirred, and a pH value of 7.5 for the liquid in the container was maintained. After the solutions A and B were both completely added into the container, stirring was performed for four hours at 70° C., and when a turbid liquid turned into emerald, it was washed to obtain a parent body. 43.5 g of $Al(NO_3)_3 \cdot 9H_2O$ was weighed to prepare an aqueous solution C at a concentration of 0.5 mol/L, and an aqueous solution D of $KHCO_3$ at a concentration of 0.5 mol/L was prepared. The aqueous solutions C and D were simultaneously added into a container containing 300 mL of deionized water at room temperature, and violently stirred, and a pH value of 7.0 for the liquid in the container was maintained. A carrier was thus obtained. Finally, the parent body and the carrier were mixed and pulped at a temperature of 70° C., which preceded solid-liquid separation. The resulting solid was washed until the conductivity of the washing liquid reached 6 μS/cm. The solid was then dried at 100° C., roasted for one hour at 450° C., and added with graphite for molding, to produce a catalyst cat. 1.

Example 2 (Comparative Example)

160.9 g of $Cu(NO_3)_2 \cdot 5H_2O$, 115.0 g of $Zn(NO_3)_2 \cdot 6H_2O$, 1.5 g of $Mg(NO_3)_2 \cdot 6H_2O$, and 1.4 g of $Ca(NO_3)_2 \cdot 4H_2O$ were weighed and dissolved into water to prepare an aqueous solution I having a concentration of 0.5 mol/L. An aqueous solution II of $K_2CO_3$ at a concentration of 0.5 mol/L was prepared. After these two solutions were preheated to 70° C., they were pumped into a blender having a passage diameter of 1,200 μm, and remained therein for 1,000 ms. A feed liquid coming from the blender directly entered a reaction tube having an inner diameter of 8 mm, and remained therein for 30 min. The blender and the reaction tube were placed in a water bath at 70° C. A feed liquid from the reaction tube, which had a pH value of 7.5, was dropwise added into a container containing 300 mL of deionized water under stirring, followed by continuous stirring of four hours at 70° C. When a turbid liquid turned into emerald, a parent body was obtained after washing. 43.5 g of $Al(NO_3)_3 \cdot 9H_2O$ was weighed to prepare an aqueous solution III having a concentration of 0.5 mol/L, and an aqueous solution IV of $KHCO_3$ at a concentration of 0.5 mol/L was prepared. The aqueous solutions III and IV were pumped into a blender at room temperature. A carrier was then prepared in a small-sized flow mixing device used in the preparation of the parent body on similar conditions, with the differences that the feed liquid from the reaction tube had a pH value of 7.0, and that the feed liquid was directly washed to produce the carrier. Finally, the parent body and the carrier were mixed and pulped at a temperature of 70° C., which preceded solid-liquid separation. The resulting solid was washed until the conductivity of the washing liquid reached 6 μS/cm. The solid was then dried at 100° C., roasted for one hour at 450° C., and added with graphite for molding, to produce a catalyst cat. 2.

Example 3

160.9 g of $Cu(NO_3)_2 \cdot 5H_2O$, 115.0 g of $Zn(NO_3)_2 \cdot 6H_2O$, 1.5 g of $Mg(NO_3)_2 \cdot 6H_2O$, and 1.4 g of $Ca(NO_3)_2 \cdot 4H_2O$ were weighed and dissolved into water to prepare an aqueous solution I having a concentration of 0.5 mol/L. An aqueous solution II of $K_2CO_3$ at a concentration of 0.5 mol/L was prepared. After these two solutions were preheated to 70° C., they were pumped into a blender having a passage diameter of 1,200 μm, and remained therein for 1,000 ms. A feed liquid coming from the blender directly entered a reaction tube having an inner diameter of 8 mm, and remained therein for 30 min. The blender and the reaction tube were placed in a water bath at 70° C., and the reaction tube was placed in an ultrasonic environment having a frequency of 40 kHz and a power of 50 W. A feed liquid from the reaction tube, which had a pH value of 7.5, was dropwise added into a container containing 300 mL of deionized water under stirring, followed by continuous stirring for four hours at 70° C. When a turbid liquid turned into emerald, a parent body was obtained after washing. 43.5 g of $Al(NO_3)_3 \cdot 9H_2O$ was weighed to prepare an aqueous solution III having a concentration of 0.5 mol/L, and an aqueous solution IV of $KHCO_3$ at a concentration of 0.5 mol/L was prepared. The aqueous solutions III and IV were pumped into a blender at room temperature. A carrier was then prepared in a small-sized flow mixing device used in the preparation of the parent body on similar conditions, with the differences that the feed liquid from the reaction tube had a pH value of 7.0, and that the feed liquid was directly washed to produce the carrier. Finally, the parent body and the carrier were mixed and pulped at a temperature of 70° C., which preceded solid-liquid separation. The resulting solid was washed until the conductivity of the washing liquid reached 6 μS/cm. The solid was then dried at 100° C., roasted for one hour at 450° C., and added with graphite for molding, to produce a catalyst cat. 3.

The results were shown in Table I. As can be seen, when the small-sized flow mixing device aided by ultrasonic waves was used to prepare the copper-zinc-based catalyst in Example 3, the catalyst performance and the hydrothermal stability of the catalyst were both improved, and were both superior to those of cat. 1 and cat. 2. Through physicochemical characterization of the catalyst, it has been found that increase of the relative amount of the aurichalcite crystalline phase in the precursor of the catalyst before being roasted was favorable for improvement of the catalytic performance and hydrothermal stability of the catalyst in the synthesis of methanol through $CO_2$ hydrogenation.

Example 4

The steps of Example 3 were used to prepare the catalyst except the following differences. In the step of preparing the parent body, after the feed liquid was dropwise added, a resulting slurry was transferred to an airtight polypropylene flask to perform hydrothermal aging for four hours at 80° C. Due to the pressure of water per se, the whole aging step was performed under pressure. When the turbid liquid turned emerald, the parent body was obtained after washing. Other steps and parameters were controlled in the same way as in Example 3. Catalyst cat. 4 was thus obtained.

The results in Table 1 show that use of the small-sized flow mixing device aided by ultrasonic irradiation and hydrothermal aging can significantly improve activity of the copper-zinc-based catalyst, and the space time yield and hydrothermal stability of methanol, in the synthesis of methanol through $CO_2$ hydrogenation.

Example 5

92.5 g of $Cu(NO_3)_2 \cdot 5H_2O$, 148.7 g of $Zn(NO_3)_2 \cdot 6H_2O$, 5.8 g of $Ba(NO_3)_2 \cdot 6H_2O$, and 71.6 g of $Zr(NO_3)_4 \cdot 5H_2O$ were weighed and dissolved into deionized water to prepare a solution A having a concentration of 0.1 mol/L. An aqueous solution B of $NaHCO_3$ at a concentration of 0.5 mol/L was prepared. After these two solutions were preheated to 40° C., they were pumped into a micro-blender having a passage diameter of 500 μm, and remained therein for 200 ms. A feed liquid coming from the micro-blender directly entered a small-sized reaction tube having an inner diameter of 1 mm, and remained therein for 10 min. The micro-blender and the small-sized reaction tube were both placed in a water bath of 40° C., and the small-sized reaction tube was placed in an ultrasonic environment at a frequency of 20 kHz and a power of 50 W. After the feed liquid from the small-sized reaction tube, which had a pH value of 7.2, was dropwise added into a container containing 250 mL of deionized water under stirring, a resulting precipitate was transferred to an airtight polypropylene flask to perform hydrothermal aging for 20 hours at 75° C. When a turbid liquid turned into emerald, solid-liquid separation was performed after aging. The resulting solid was washed until the conductivity of the washing liquid reached 9 μS/cm. The solid was then dried at 100° C., roasted for two hours at 350° C., and added with graphite for molding, to produce a catalyst cat. 5.

Example 6

77.7 g of $Cu(NO_3)_2 \cdot 5H_2O$, 83.3 g of $Zn(NO_3)_2 \cdot 6H_2O$, 3.6 g of $Ce(NO_3)_3 \cdot 6H_2O$, 3.6 g of $Nd(NO_3)_3 \cdot 6H_2O$, and 57.2 g of $C_{16}H_{36}O_4Ti$ were weighed and dissolved into ethanol to prepare an alcoholic solution A having a concentration of 0.05 mol/L. An aqueous solution B containing 0.5 mol/L NaOH and 0.5 mol/L $Na_2CO_3$ was prepared. After these two solutions were preheated to 60° C., they were pumped into a micro-blender having a passage diameter of 1,000 μm, and remained therein for 50 ms. A feed liquid coming from the micro-blender directly entered a small-sized reaction tube having an inner diameter of 5 mm, and remained therein for 15 min. The micro-blender and the small-sized reaction tube were both placed in a water bath of 60° C., and the small-sized reaction tube was placed in an ultrasonic environment at a frequency of 30 kHz and a power of 200 W. After the feed liquid from the small-sized reaction tube, which had a pH value of 7.0, was dropwise added into a container containing 300 mL of deionized water under stirring, a resulting precipitate was transferred to an airtight polypropylene flask to perform aging for 24 hours at 60° C. When a turbid liquid turned into emerald, solid-liquid separation was performed after aging. The resulting solid was washed until the conductivity of the washing liquid reached 6 μS/cm. The solid was then dried at 100° C., roasted for two hours at 400° C., and added with graphite for molding, to produce a catalyst cat. 6.

Example 7

138.8 g of $Cu(NO_3)_2 \cdot 5H_2O$, 63.7 g of $Zn(NO_3)_2 \cdot 6H_2O$, and 8.2 g of $Pr(NO_3)_3 \cdot 6H_2O$ were weighed and dissolved into water to prepare an aqueous solution I having a concentration of 1 mol/L. An aqueous solution II of $NaHCO_3$ and KOH both at a concentration of 0.5 mol/L was prepared. After these two solutions were preheated to 75° C., they were pumped into a micro-blender having a passage diameter of 2,000 μm, and remained therein for 800 ms. A feed liquid coming from the micro-blender directly entered a small-sized reaction tube having an inner diameter of 5 mm, and remained therein for 40 min. The micro-blender and the small-sized reaction tube were both placed in a water bath of 75° C., and the small-sized reaction tube was placed in an ultrasonic environment at a frequency of 20 kHz and a power of 500 W. After the feed liquid from the small-sized reaction tube, which had a pH value of 7.5, was dropwise added into a container containing 200 mL of deionized water under stirring, a resulting precipitate was transferred to an airtight polypropylene flask to perform aging for 10 hours at 75° C. A turbid liquid turned into emerald, and a binary parent body was obtained after aging. 150.1 g of $Al(NO_3)_3 \cdot 9H_2O$ was weighed to prepare an aqueous solution III having a concentration of 1 mol/L, and an aqueous solution IV of $KHCO_3$ at a concentration of 1 mol/L was prepared. The aqueous solutions III and IV were pumped into a micro-blender at room temperature. A carrier was then prepared in a small-sized flow mixing device used in the preparation of the binary parent body on similar conditions, with the differences that the feed liquid from the small-sized reaction tube had a pH value of 7.0, and that the feed liquid was directly washed without being aged, to produce the carrier. Finally, the parent body and the carrier were mixed and pulped at a temperature of 75° C., which preceded solid-liquid separation. The resulting solid was washed until the conductivity of the washing liquid reached 8 μS/cm. The solid was then dried at 100° C., roasted for one hour at 500° C., and added with graphite for molding, to produce a catalyst cat. 7.

Examples 5-7 proved that, different promoters performed different promoting functions on the copper-zinc-based catalysts in the synthesis of methanol through $CO_2$ hydrogenation. This relates to dispersion of the promoters on the surface of the catalysts, alkalinity thereof, and alkaline sites provided thereby.

Example 8

69.4 g of $Cu(NO_3)_2 \cdot 5H_2O$, 173.5 g of $Zn(NO_3)_2 \cdot 6H_2O$, 10.8 g of $La(NO_3)_3 \cdot 6H_2O$, and 93.8 g of $Al(NO_3)_3 \cdot 9H_2O$ were weighed and dissolved into deionized water to prepare a solution A having a concentration of 0.02 mol/L. An aqueous solution B of $Na_2CO_3$ at a concentration of 0.05 mol/L was prepared. After these two solutions were preheated to 50° C., they were pumped into a micro-blender having a passage diameter of 50 μm, and remained therein for 5 ms. A feed liquid coming from the micro-blender directly entered a small-sized reaction tube having an inner diameter of 0.5 mm, and remained therein for 5 min. The micro-blender and the small-sized reaction tube were both placed in a water bath of 50° C., and the small-sized reaction tube was placed in an ultrasonic environment at a frequency of 20 kHz and a power of 100 W. After a feed liquid from the small-sized reaction tube, which had a pH value of 8.0, was dropwise added into a container containing 200 mL of deionized water under stirring, a resulting precipitate was transferred to an airtight polypropylene flask to perform hydrothermal aging for 10 hours at 80° C. When a turbid liquid gradually turned into emerald, solid-liquid separation was performed after aging. The resulting solid was washed until the conductivity of the washing liquid reached 7 μS/cm. The solid was then dried at 100° C., roasted for two hours at 300° C., and added with graphite for molding, to produce a catalyst cat. 8.

Example 9 (Comparative Example)

69.4 g of $Cu(NO_3)_2 \cdot 5H_2O$, 173.5 g of $Zn(NO_3)_2 \cdot 6H_2O$, 10.8 g of $La(NO_3)_3 \cdot 6H_2O$, and 93.8 g of $Al(NO_3)_3 \cdot 9H_2O$ were weighed and dissolved into deionized water to prepare a solution A having a concentration of 0.02 mol/L. An aqueous solution B of $Na_2CO_3$ at a concentration of 0.05 mol/L was prepared. After these two solutions were preheated to 50° C., they were simultaneously added into a container containing 200 mL of deionized water at 50° C. under violent stirring. The resulting liquid in the container was maintained at a pH value of 7.2, and was stirred for 60 min at 50° C. When a turbid liquid turned into emerald, solid-liquid separation was performed after aging. The resulting solid was washed until the conductivity of the washing liquid reached 7 μS/cm. The solid was then dried at 100° C., roasted for two hours at 300° C., and added with graphite for molding, to produce a catalyst cat. 9.

Example 10

160.9 g of $Cu(NO_3)_2 \cdot 5H_2O$, 115.0 g of $Zn(NO_3)_2 \cdot 6H_2O$, 1.5 g of $Mg(NO_3)_2 \cdot 6H_2O$, and 1.4 g of $Ca(NO_3)_2 \cdot 4H_2O$ were weighed and dissolved into water to prepare an aqueous solution I having a concentration of 0.5 mol/L. An aqueous solution II of $K_2CO_3$ at a concentration of 0.5 mol/L was prepared. After these two solutions were preheated to 70° C., they were dropwise added into a container containing 300 mL of deionized water at 70° C. under violent stirring, and the container was placed in an ultrasonic environment having a frequency of 40 kHz and a power of 50 W. The liquid in the container was maintained at a pH value of 7.5. Afterwards, stirring was continued for four hours at 70° C. When a turbid liquid turned into emerald, a parent body was obtained after washing. 43.5 g of $Al(NO_3)_3 \cdot 9H_2O$ was weighed to prepare an aqueous solution III having a concentration of 0.5 mol/L, and an aqueous solution IV of $KHCO_3$ at a concentration of 0.5 mol/L was prepared. The aqueous solutions III and IV were simultaneously added into a container containing 300 mL of deionized water at room temperature under violent stirring. The liquid in the container was maintained at a pH value of 7.0. A carrier was then obtained. Finally, the parent body and the carrier were mixed and pulped at a temperature of 70° C., which preceded solid-liquid separation. The resulting solid was washed until the conductivity of the washing liquid reached 6 μS/cm. The solid was then dried at 100° C., roasted for one hour at 450° C., and added with graphite for molding, to produce a catalyst cat. 10.

The conditions for activity test were as follows. The activity of cats. 1-10 were assessed in a fixed bed microreactor. Each of the catalysts, with a granularity ranged from 20 to 40 meshes and at a filling amount of 2 mL, was performed in-situ reduction in a reactor by a gas mixture of $H_2/N_2$ containing 5% of $H_2$. The temperature in the end of the reduction was 240° C. The volume ratio of $H_2/CO_2$ in the feed gasses was 3:1, and the reaction was performed at a pressure of 5 MPa and a space velocity of $1 \times 10^4$ h$^{-1}$. The assessment was performed at a temperature of 240° C., and the original performance was tested after the reaction remained stable for 4 hours. Heat treatment was then performed on the catalyst for 5 hours in the atmosphere of $N_2$—$H_2O$ (which was produced by bubbling water at 100° C. with $N_2$), at 350° C. and atmospheric pressure. The above conditions for activity assessment were regained and maintained stable for two hours, which preceded test of performance after heat resistance. The product was analyzed by gas chromatograph, and the results were shown in Table 1, in which, the hydrothermal stability=yield of methanol after heat resistance/the original yield of methanol*100%. Reference can be made to Table 1 for specific data.

TABLE 1

Assessment results of performances of the catalysts in the synthesis of methanol through $CO_2$ hydrogenation

| Catalyst | Main crystalline phase's composition of the precursor before roasting [a] | $I_{M/(A+R)}$ or $I_{LDHs/(A+R)}$ [b] | $I_{A/R}$ [c] | Specific surface area of Cu/(m$^2$/g) | Specific surface area of Cu × percent of Cu | Original performance Conversion of $CO_2$/% | Original performance Space time yield of methanol/ (g/h/mL) | Performance after heat resistance Conversion of $CO_2$/% | Performance after heat resistance Space time yield of methanol/ (g/h/mL) | Hydrothermal stability/% |
|---|---|---|---|---|---|---|---|---|---|---|
| cat. 1 | R + A + M | 0.187 | 0.126 | 18 | 8.89 | 22.2 | 0.46 | 12.9 | 0.25 | 54.3 |
| cat. 2 | R + A + M | 0.179 | 0.130 | 19 | 9.50 | 23.9 | 0.50 | 15.8 | 0.29 | 58.1 |
| cat. 9 | R + A + LDHs | 0.152 | 0.102 | 22 | 4.26 | 20.0 | 0.40 | 12.1 | 0.23 | 57.5 |
| cat. 10 | R + A + M | 0.062 | 0.290 | 25 | 12.34 | 24.2 | 0.53 | 16.9 | 0.32 | 60.2 |
| cat. 3 | A + R + M | 0.103 | 0.327 | 28 | 13.83 | 23.9 | 0.57 | 21.8 | 0.37 | 65.9 |
| cat. 4 | A + R + M | 0.058 | 0.382 | 32 | 15.80 | 29.8 | 0.69 | 27.3 | 0.61 | 88.2 |
| cat. 5 | A + R + M | 0.120 | 0.296 | 38 | 10.92 | 27.1 | 0.64 | 25.4 | 0.51 | 79.2 |
| cat. 6 | A + R + M | 0.119 | 0.435 | 41 | 14.91 | 33.2 | 0.81 | 31.7 | 0.66 | 82.0 |

TABLE 1-continued

Assessment results of performances of the catalysts in the synthesis of methanol through $CO_2$ hydrogenation

| Catalyst | Main crystalline phase's composition of the precursor before roasting [a] | $I_{M/(A+R)}$ or $I_{LDHs/(A+R)}$ [b] | $I_{A/R}$ [c] | Specific surface area of Cu/(m$^2$/g) | Specific surface area of Cu × percent of Cu | Original performance | | Performance after heat resistance | | Hydrothermal stability/% |
|---|---|---|---|---|---|---|---|---|---|---|
| | | | | | | Conversion of $CO_2$/% | Space time yield of methanol/ (g/h/mL) | Conversion of $CO_2$/% | Space time yield of methanol/ (g/h/mL) | |
| cat. 7 | A + R + M | 0.109 | 0.287 | 34 | 12.77 | 25.3 | 0.56 | 19.8 | 0.46 | 82.1 |
| cat. 8 | R + A + LDHs | 0.091 | 0.332 | 52 | 10.01 | 26.8 | 0.66 | 24.2 | 0.51 | 77.2 |

[a] LDHs represents $(Cu^{2+},Zn^{2+})$—$Al^{3+}$—$CO_3^{2-}$ (hydrotalcite crystalline phase); R represents $(Cu,Zn)_2CO_3(OH)_2$ (rosasite crystalline phase); A represents $(Cu,Zn)_5(CO_3)_2(OH)_6$ (aurichalcite crystalline phase); and M represents $(Cu)_2CO_3(OH)_2$ (malachite crystalline phase).
[b] $I_{M/(A+R)}$ represents a ratio of diffraction peak intensity at 2θ of about 31.9° of M to the sum of diffraction peak intensity at 2θ of about 33.0° of A and diffraction peak intensity at 2θ of about 17.3° of R in an X-ray diffraction pattern of the precursor prior to roasting of the catalyst. Likewise, $I_{LDHs/(A+R)}$ represents a ratio of diffraction peak intensity at 2θ of about 11.7° of LDHs to the sum of diffraction peak intensity at 2θ of about 33.0° of A and diffraction peak intensity at 2θ of about 17.3° of R in the X-ray diffraction pattern of the precursor prior to roasting of the catalyst.
[c] $I_{A/R}$ represents a ratio of diffraction peak intensity at 2θ of about 33.0° of A to diffraction peak intensity at 2θ of about 17.3° of R in the X-ray diffraction pattern of the precursor prior to roasting of the catalyst.

The ratios between diffraction peak intensities of different copper-zinc-based complex salts are positively correlated to the ratios of contents of the corresponding complex salts in the precursor. The data in Table 1 indicate that, under given reaction conditions, the copper-zinc-based catalysts prepared according to the method of the present disclosure all present superior catalytic performance and hydrothermal stability in the synthesis of methanol through $CO_2$ hydrogenation.

Compared with cats. 1 and 9 prepared according to the conventional precipitation method, regarding cat. 10 prepared according to the method provided in the present disclosure, the specific surface area of the metal copper in the reduced state catalyst was relatively high, and the amount of the aurichalcite crystalline phase in the catalyst precursor was significantly increased (the value of $I_{A/R}$ was increased), while the amount of the malachite crystalline phase was decreased. This indicated a deepened degree of isomorphous substitution between copper and zinc in the precursor, an increased interaction therebetween, and improvement of the catalytic performance and hydrothermal stability of the catalyst. This is also clear from comparisons between cat. 3 and cat. 2.

Meanwhile, when the small-sized flow mixing device was used in combination with assistance of ultrasonic waves to prepare the catalysts (cat. 5, cat. 6, and cat. 3), the active precursors obtained contained significantly improved amounts of the aurichalcite crystalline phase (the value of $I_{A/R}$ was increased) and decreased amounts of the malachite crystalline phase. This indicated a deepened degree of isomorphous substitution between copper and zinc in the precursors, increased interaction therebetween, increased specific surface area of copper in the reduced state catalysts, and constant improvement of the catalytic performance and hydrothermal stability of the catalysts.

Finally, aided by hydrothermal aging (cat. 4, cat. 7, and cat. 8), the amounts of active aurichalcite crystalline phase and the specific surface area of copper in the reduced state catalysts were both further improved, and the catalytic performance of the catalysts, especially the hydrothermal stability of the catalysts was significantly improved. The examples showed that introduction of different alkaline oxides into the copper-zinc-based catalysts through the method of the present disclosure enables the catalysts to present superior catalytic performance and hydrothermal stability in the synthesis of methanol through $CO_2$ hydrogenation.

To conclude the above, according to the present disclosure, at the outset, ultrasonic waves can be used as assistance to control types of crystals in the precursor before roasting of the catalyst. This can increase the amount of the aurichalcite crystalline phase (A) in the creative precursor used in the synthesis of methanol through $CO_2$ hydrogenation, thereby improving the catalytic performance of the catalyst. Moreover, the small-sized flow mixing device was further used to improve the specific surface area of the copper in the reduced state catalyst, so as to improve the performance of the catalyst. In addition, hydrothermal aging was further employed to promote fine development of the crystal form of the aurichalcite crystalline phase (A), thereby further improving the catalytic performance of the catalyst, and largely improving the hydrothermal stability of the copper-zinc-based catalyst in the synthesis of methanol through $CO_2$ hydrogenation.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 50 to 90, it is intended that values such as 51 to 89, 52 to 88 . . . 69 to 71, 70 to 71 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

It should be noted that the above examples are only used to explain, rather than to limit the present disclosure in any manner. Although the present disclosure has been discussed with reference to preferable examples, it should be understood that the terms and expressions adopted are for describing and explaining instead of limiting the present disclosure. The present disclosure can be modified within the scope of the claims, or can be amended without departing from the scope or spirits of the present disclosure. Although the present disclosure is described with specific methods, materials, and examples, the scope of the present disclosure herein disclosed should not be limited by the particularly disclosed examples as described above, but can be extended to other methods and uses having the same functions.

The invention claimed is:
1. A method for preparing a copper-zinc-based catalyst used in synthesis of methanol through $CO_2$ hydrogenation, comprising the following steps:

step S1: preparing an aqueous solution containing a copper salt, a zinc salt, and a metal salt promoter, and blending said aqueous solution and an aqueous solution of a precipitator, to produce a first feed liquid, imposing radiation of ultrasonic waves on the first feed liquid thereby generating a first reaction product, aging, solid-liquid separating, and washing the first reaction product to produce a parent body;

step S2: preparing a solution of a carrier precursor, which is blended with the aqueous solution of a precipitator, to produce a second feed liquid, imposing radiation of ultrasonic waves on the second feed liquid thereby generating a second product, stirring, solid-liquid separating, and washing the second product to produce a carrier material; and step S3: blending and then stirring the parent body and the carrier material, to generate a third product, solid-liquid separating, washing, and drying to produce a catalyst precursor, followed by roasting of the catalyst precursor to obtain the catalyst, wherein said aging of the first reaction product is hydrothermal aging performed for 4 to 24 hours under airtight conditions at a temperature in the range from 60 to 80° C.

2. The method according to claim 1, wherein the ultrasonic waves have a frequency in the range from 20 to 40 kHz, and a power in the range from 50 to 500 W.

3. The method according to claim 1, wherein said blending and/or reaction in steps S1 and S2 are performed each time at a temperature in the range from 40 to 75° C.

4. The method according to claim 1, wherein said blending in steps S1 and S2 is performed each time in a blender having a passage diameter in the range from 50 to 2000 μm, and a residence time of the first and second feed liquids in the blender ranges from 5 to 1,000 ms; and/or wherein said reaction is performed each time in a reaction tube having an inner diameter in the range from 0.5 to 8 mm, and a residence time of the first and second feed liquids in the reaction tube ranges from 5 to 40 min.

5. The method according to claim 1, wherein main crystalline phase's composition of the catalyst precursor comprises rosasite crystalline phase, aurichalcite crystalline phase, and malachite crystalline phase, wherein:

the ratio of X-ray diffraction peak intensity of the malachite crystalline phase to the sum of X-ray diffraction peak intensity of the rosasite crystalline phase and X-ray diffraction peak intensity of the aurichalcite crystalline phase is in the range from 0.05:1 to 0.12:1; and the ratio of the X-ray diffraction peak intensity of the aurichalcite crystalline phase to the X-ray diffraction peak intensity of the rosasite crystalline phase is in the range from 0.25:1 to 0.45:1.

6. The method according to claim 1, wherein: the aqueous solution containing a copper salt, a zinc salt, and a metal salt promoter is an aqueous solution of copper-nitrate, zinc-nitrate, and a metal nitrate promoter; or the metal nitrate salt promoter comprises at least one selected from the group consisting of alkaline earth metal salts and rare earth element salts; or the carrier precursor is at least one selected from the group consisting of aluminum nitrate, zirconium nitrate, and tetrabutyl titanate.

7. The method according to claim 1, wherein:

the zinc salt is used at such an amount that the molar ratio of copper to zinc in the catalyst is in the range from 3:7 to 7:3; or the metal nitrate salt promoter is used at such an amount that the molar ratio of the promoter in total to the element of copper in the catalyst is (0.05-0.1):1; or the carrier precursor is used at such an amount that the molar ratio of the carrier in total to the element of copper in the catalyst is (0.1-1):1.

8. The method according to claim 1, wherein the precipitator comprises at least one selected from the group consisting of sodium carbonate, sodium bicarbonate, potassium carbonate, and potassium bicarbonate; or a mixture of at least one selected from the group consisting of sodium carbonate, sodium bicarbonate, potassium carbonate, and potassium bicarbonate, and at least one selected from the group consisting of sodium hydroxide and potassium hydroxide, wherein when the precipitator comprises a mixture of at least one selected from the group consisting of sodium carbonate, sodium bicarbonate, potassium carbonate, and potassium bicarbonate, and at least one selected from the group consisting of sodium hydroxide and potassium hydroxide, the molar ratio of the at least one selected from the group consisting of sodium carbonate, sodium bicarbonate, potassium carbonate, and potassium bicarbonate to the at least one selected from the group consisting of sodium hydroxide and potassium hydroxide is not lower than 1:3; or wherein the aqueous solution of a precipitator has a concentration of the precipitator in the range from 0.05 to 1 mol/L.

9. A method for preparing a copper-zinc-based catalyst used in synthesis of methanol through $CO_2$ hydrogenation, comprising: preparing a solution containing a copper salt, a zinc salt, a metal salt promoter, and a carrier precursor, and blending said solution and an aqueous solution of a precipitator, to produce a third feed liquid, imposing radiation of ultrasonic waves on the third feed liquid, thereby generating a third product, stirring, aging, solid-liquid separating, washing, and drying the third product to produce a catalyst precursor, followed by roasting the catalyst precursor to obtain the catalyst, wherein said aging of the third product is hydrothermal aging performed for 4 to 24 hours under airtight conditions at a temperature in a range from 60 to 80° C.

10. The method according to claim 9, wherein the ultrasonic waves have a frequency in the range from 20 to 40 kHz, and a power in the range from 50 to 500 W.

11. The method according to claim 9, wherein said blending and/or reaction are performed at a temperature in the range from 40 to 75° C.

12. The method according to claim 9, wherein said blending is performed in a blender having a passage diameter in the range from 50 to 2,000 μm, and a residence time of the third feed liquid in the blender ranges from 5 to 1,000 ms; and/or wherein said reaction is performed in a reaction tube having an inner diameter in the range from 0.5 to 8 mm, and a residence time of the third feed liquid in the reaction tube ranges from 5 to 40 min.

13. The method according to claim 9, wherein main crystalline phase's composition of the catalyst precursor comprises rosasite crystalline phase, aurichalcite crystalline phase, and malachite crystalline phase, or alternatively comprises rosasite crystalline phase, aurichalcite crystalline phase, and hydrotalcite crystalline phase, wherein:

the ratio of X-ray diffraction peak intensity of the malachite crystalline phase or X-ray diffraction peak intensity of the hydrotalcite crystalline phase to the sum of X-ray diffraction peak intensity of the rosasite crystalline phase and X-ray diffraction peak intensity of the aurichalcite crystalline phase is in the range from 0.05:1 to 0.12:1; and the ratio of the X-ray diffraction peak intensity of the aurichalcite crystalline phase to the X-ray diffraction peak intensity of the rosasite crystalline phase is in the range from 0.25:1 to 0.45:1.

14. The method according to claim 9, wherein: the solution containing a copper salt, a zinc salt, and a metal salt promoter is a solution of copper-nitrate, zinc-nitrate, and a metal nitrate promoter; or the metal salt promoter comprises at least one selected from the group consisting of alkaline earth metal salts and rare earth element salts; or the carrier precursor is at least one selected from the group consisting of aluminum nitrate, zirconium nitrate, and tetrabutyl titanate.

15. The method according to claim 9, wherein:

the zinc salt is used at such an amount that the molar ratio of copper to zinc in the catalyst is in the range from 3:7 to 7:3; or the metal salt promoter is used at such an amount that the molar ratio of the promoter in total to the element of copper in the catalyst is (0.05-0.1):1; or the carrier precursor is used at such an amount that the molar ratio of the carrier in total to the element of copper in the catalyst is (0.1-1):1.

16. The method according to claim 9, wherein the precipitator comprises at least one selected from the group consisting of sodium carbonate, sodium bicarbonate, potassium carbonate, and potassium bicarbonate; or a mixture of at least one selected from the group consisting of sodium carbonate, sodium bicarbonate, potassium carbonate, and potassium bicarbonate, and at least one selected from the group consisting of sodium hydroxide and potassium hydroxide, wherein when the precipitator comprises a mixture of at least one selected from the group consisting of sodium carbonate, sodium bicarbonate, potassium carbonate, and potassium bicarbonate, and at least one selected from the group consisting of sodium hydroxide and potassium hydroxide, the molar ratio of the at least one selected from the group consisting of sodium carbonate, sodium bicarbonate, potassium carbonate, and potassium bicarbonate to the at least one selected from the group consisting of sodium hydroxide and potassium hydroxide is not lower than 1:3; or wherein the aqueous solution of a precipitator has a concentration of the precipitator in the range from 0.05 to 1 mol/L.

17. A copper-zinc-based catalyst used in synthesis of methanol through $CO_2$ hydrogenation prepared according to the method of claim 1, wherein the catalyst is reduced to generate a reduced state catalyst, in which a product of a mass percent of the metal copper and a specific surface area of the metal copper is in the range from 10 to 20 $m^2/g$.

18. A copper-zinc-based catalyst used in synthesis of methanol through $CO_2$ hydrogenation prepared according to the method of claim 9, wherein the catalyst is reduced to generate a reduced state catalyst, in which a product of a mass percent of the metal copper and a specific surface area of the metal copper is in the range from 10 to 20 $m^2/g$.

* * * * *